(12) United States Patent
Cheng et al.

(10) Patent No.: US 11,116,708 B2
(45) Date of Patent: *Sep. 14, 2021

(54) PERSONAL CARE COMPOSITIONS INCLUDING NARINGIN:ZINC COMPLEXES AND METHODS FOR THE SAME

(71) Applicant: Colgate-Palmolive Company, New York, NY (US)

(72) Inventors: Shujiang Cheng, Warren, NJ (US); Zeenat Nabi, Cranbury, NJ (US); Laurence Du-Thumm, Princeton, NJ (US); Qiang Wu, Hillsborough, NJ (US); Jane Ong, Franklin Park, NJ (US); Halyna Siomyk, Cliffside Park, NJ (US); Harsh Mahendra Trivedi, Hillsborough, NJ (US); James Masters, Ringoes, NJ (US); Chi-Yuan Cheng, Hillsborough, NJ (US); Donghui Wu, Bridgewater, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/758,434

(22) PCT Filed: Dec. 19, 2017

(86) PCT No.: PCT/US2017/067407
§ 371 (c)(1),
(2) Date: Apr. 23, 2020

(87) PCT Pub. No.: WO2019/083554
PCT Pub. Date: Feb. 5, 2019

(65) Prior Publication Data
US 2020/0246242 A1    Aug. 6, 2020

Related U.S. Application Data

(63) Continuation-in-part of application No. PCT/US2017/057997, filed on Oct. 24, 2017.

(51) Int. Cl.
*A61K 8/27* (2006.01)
*A61K 8/49* (2006.01)
*A61K 8/60* (2006.01)
*A61Q 15/00* (2006.01)
*A61Q 19/08* (2006.01)
*A61Q 19/02* (2006.01)
*A61Q 11/00* (2006.01)

(52) U.S. Cl.
CPC .............. *A61K 8/27* (2013.01); *A61K 8/498* (2013.01); *A61K 8/602* (2013.01); *A61Q 15/00* (2013.01); *A61Q 19/02* (2013.01); *A61Q 19/08* (2013.01); *A61K 2800/51* (2013.01); *A61K 2800/58* (2013.01); *A61Q 11/00* (2013.01)

(58) Field of Classification Search
None
See application file for complete search history.

(56) References Cited

U.S. PATENT DOCUMENTS

| 7,598,291 | B2 | 10/2009 | Han | |
| 10,213,374 | B2* | 2/2019 | Ong | A61K 8/27 |
| 10,548,829 | B2* | 2/2020 | Ong | A61K 8/27 |
| 2004/0053858 | A1* | 3/2004 | Berg | A61K 2300/00 514/27 |
| 2015/0150770 | A1 | 6/2015 | Morariu | |
| 2018/0110712 | A1* | 4/2018 | Ong | A61K 8/27 |
| 2019/0231667 | A1* | 8/2019 | Ong | A61K 8/27 |

FOREIGN PATENT DOCUMENTS

| CN | 102218021 | 10/2011 |
| CN | 105232388 | 1/2016 |
| EP | 0455432 | 11/1991 |
| EP | 1327438 | 7/2003 |
| RU | 2159611 | 11/2000 |
| RU | 2209620 | 8/2003 |
| WO | 2015/027308 | 3/2015 |

OTHER PUBLICATIONS

AL-Hassani et al., 2015, "Synthesis, Characterization, Theoretical Studies and Biological Activities of Naringin Metal Complexes," Acta Chimica & Pharmaceutica Indica 5(3):129-142.
Ang et al., 2011, "Naringin abrogates osteoclastogenesis and bone resorption via the inhibition of RANKL-induced NF-KB and ERK activation," FEBS Letters 585(17):2755-2762.
Bharti et al., 2014, "Preclinical Evidence for the Pharmacological Actions of Naringin: A Review," Planta Medica 80 (6):437-451.
Brandt, 2013, "The clinical effects of zinc as a topical or oral agent on the clinical response and pathophysiologic mechanisms of acne: a systematic review of the literature," J. Drugs Dermatol. 12(5):542-545.
Darby et al., 2001, "Microbiology of periodontal disease in children and young adults," Periodontology 2000 26:33-53.
Epasinghe et al., 2016, "Effect of Flavonoids on Remineralization of Artificial Root Caries," Australian Dental Journal 61(2):196-202.
Internationl Search Report and Written Opinion of the International Searching Authority in International Application No. PCT/US2017/057997, dated Jan. 5, 2018.
Kandhare et al., 2014, "Naringin, a Flavanone Glycoside, Promotes Angiogenesis and Inhibits Endothelial Apoptosis Through Modulation of Inflammatory and Growth Factor Expression in Diabetic Foot Ulcer in Rats," Chemico-Biological Interactions 219:101-112.
Kiefer et al., 2010, "Citrus Flavonoids with Skin Lightening Effects—Safety and Efficacy Studies," SOFW Journal Dec. 2010 pp. 45-54.
Kuntic et al., 1998, "Spectrophotometric Investigation of Uranil(II)-Rutin Complex in 70 Ethanol," J. Agric. Food Chem. 46(12):5139-5142.

(Continued)

*Primary Examiner* — Sin J Lee

(57) ABSTRACT

Personal care compositions including a naringin:zinc complex and methods for preparing and using the same are provided. The personal care compositions may include a carrier and a naringin:zinc complex having a 2:1 naringin to zinc molar ratio.

5 Claims, No Drawings

(56) References Cited

OTHER PUBLICATIONS

Li et al., 2007, "Infrared and DNA-binding on ultraviolet and fluorescence spectra of new copper and zinc complexes with a naringenin Schiff-base ligand," Spectrochimica Acla Part A 67(2):395-401.

Li et al., 2014, "The remineralisation of enamel: a review of the literature," J. of Dentistry 42:S12-S20.

Malesev et al., 2007, "Investigation of metal-?flavonoid chelates and the determination of flavonoids via metal-? flavonoid complxing reactions," J. Serb. Chem. Soc. 72(10):921-939.

Misiak et al., 2010, "Interactions of Flavonoids with Transition Metal Ions," Pharmaceuticals 39-42.

Pereira et al., 2007, "Synthesis and Characterization of a Metal Complex Containing Naringin and Cu, and its Antioxidant, Antimicrobial, Antiinflammatory and Tumor Cell Cytotoxicity," Molecules12(7):1352-1366.

Sarria et al., 2016, "Copper (II) and zinc (II) complexes with flavanone derivatives: Identification of potential cholinesterase inhibitors by on-flow assays," J. Inorganic Biochemistry 164:141-149.

Selvaraj, 2014, "Investigations on the Membrane Interactions of Narignin and its Complexes with Copper and Iron: Implications for Their Cytotoxicity," RSC Advances4(87):46407-46417.

Toledano et al., 2012, "Zinc-Inhibited MMP-Mediated Collagen Degradation after Different Dentine Demineralization Procedures," Caries Research 46(3):201-207.

Tsui et al., 2008, "The inhibitory effects of naringin on the growth of periodontal pathogens in vitro," Research Phytotherapy 22(3):401-406.

Yousuf, 2014, "Binding of the Bi (III) Complex of Naringin with ß-Cyclodextrin/Calf Thymus DNA: Absorption and Fluorescence Characteristics," Intl Journal of Spectroscopy, Article ID 562160.

AL-Hassani et al., 2015, "Synthesis, characterization, theoretical Studies and biological activities of naringin metal complexes," Acta Chim. Pharm. Indica 5(3):129-142 Retrieved from the Internet: URL:http://www.tsijournals.com/articles/synthesis-characterization-theoretical-studies-and-biological-activities-of-naringin-metal-complexes.pdf.

International Search Report and Written Opinion of the International Searching Authority in International Application No. PCT/US2017/067407, dated May 7, 2018.

Sarria et al., 2016, "Copper (II) and zinc (II) complexes with flavanone derivatives: Identification of potential cholinesterase inhibitors by on-flow assays," Journal of Inorganic Biochemistry 164(17):141-149.

Vshivkov S. A., Tyukova I. S. Educational and methodological complex of the discipline "Technology for obtaining composite polymer nanomaterials" [Electronic resource]/S.A. Vshivkov., I.S. Tyukova; Min-vo obrazovaniya i nauki RF, Ural. gos. un-t im. A. M. Gor'kogo.—Elektron. dan.—Ekaterinburg, 2011. (link: https://elar.urfu.ru/handle/10995/3568/).https://elar.urfu.ru/bitstream/10995/3568/11/1358540_lectures_ch_1.pdf, found on the Internet, Wayback Internet Archive Machine, Oct. 20, 2016, pp. 1-132. in Russian with English translation.

* cited by examiner

PERSONAL CARE COMPOSITIONS INCLUDING NARINGIN:ZINC COMPLEXES AND METHODS FOR THE SAME

CROSS-REFERENCE TO RELATED APPLICATIONS

This application is a national stage entry under 35 U.S.C. § 371 of International Patent Application No. PCT/US2017/067407, filed Dec. 19, 2017, which claims priority to PCT Application No. PCT/US2017/057997, which was filed Oct. 24, 2017, the disclosures of which are incorporated by reference to the extent consistent with the present application.

BACKGROUND

Signs of aging often appear on the skin as, among others, fine lines and wrinkles, age spots, dryness, blotchy discolorations, and sagging. Similarly, signs of aging may also manifest in the hair as frizziness, dullness, and loss of hair. These signs of aging or damage to the skin and hair are often exacerbated by other factors, such as diet, stress, environmental pollution, sun exposure, contact with chemicals (e.g., household chemicals), and the like.

Numerous personal care products or compositions thereof have been developed for the skin and hair to prevent or treat the signs of aging. For example, conventional personal care products often incorporate one or more benefit or therapeutic agents, such as taurine, that may facilitate the regeneration or healing of the skin and hair to counter the damage or signs of aging. While many benefit agents have been identified and utilized, the search for new benefit agents exhibiting improved results is ongoing.

What is needed, then, are improved personal care products and compositions thereof, and methods for regenerating and preventing inflammation of skin with the same.

BRIEF SUMMARY

This summary is intended merely to introduce a simplified summary of some aspects of one or more implementations of the present disclosure. Further areas of applicability of the present disclosure will become apparent from the detailed description provided hereinafter. This summary is not an extensive overview, nor is it intended to identify key or critical elements of the present teachings, nor to delineate the scope of the disclosure. Rather, its purpose is merely to present one or more concepts in simplified form as a prelude to the detailed description below.

Embodiments of the disclosure may provide a personal care composition including a carrier and a naringin:zinc complex. The naringin:zinc complex may have a 2:1 naringin to zinc molar ratio.

In at least one embodiment, the naringin:zinc complex may have a melting point greater than or equal to 230° C., greater than or equal to 250° C., or greater than or equal to 280° C.

In at least one embodiment, the naringin:zinc complex may have a diffusion coefficient of from about 2.8E−11 m$^2$/s to about 3.2E−11 m$^2$/s in dimethyl sulfoxide and at 25° C.

In at least one embodiment, the naringin:zinc complex may be present in an amount of from about 0.01 weight % to about 5 weight %, preferably about 0.5 weight % to about 4.5 weight %, more preferably about 1.6 weight % to about 3.4 weight %, based on a total weight of the personal care composition.

In at least one embodiment, the naringin:zinc complex may be dispersed in the carrier.

In at least one embodiment, the personal care composition may be an antiperspirant, a deodorant, a body wash, a shower gel, a soap, a face wash, a shampoo, a hair conditioner, a lotion, a moisturizer, a serum, a spot treatment, or a cosmetic.

In at least one embodiment, the personal care composition may be a skin care product, and the carrier may include at least one of surfactants, conditioning agents, moisturizers, sunscreens, UV absorbers, antioxidants, enzymes and other proteins, vitamins, antibacterial agents, odor reducing agents, steroids, anti-inflammatory agents, naturally and non-naturally occurring humectants, skin lipid fluidizers, occlusive agents, amino acids, physical and chemical exfoliants, skin whiteners, anti-aging, antiperspirant actives, and mixtures thereof.

In at least one embodiment, the personal care composition may be a hair care product, and the carrier may include at least one of surfactants, colorants, denaturants, film forming polymers, conditioning agents, fixatives, hair color stabilizers, anti-inflammatory agents, antioxidants, moisturizers, enzymes and other proteins, vitamins, antidandruff agents, sunscreen agents, and mixtures thereof.

In at least one embodiment, the personal care composition may be an antiperspirant or a deodorant, and the carrier may include at least one of fragrances, alcohols, antimicrobial agents, antiperspirant salts, odor reducing agents, moisturizers, and mixtures thereof.

In at least one embodiment, the personal care composition may be a cleansing composition, and the carrier may include at least one of fragrances, essential oils, emulsifying agents, thickening agents, colorants, surfactants, natural actives, therapeutic actives, stain prevention actives, antimicrobial agents, vitamins, natural extracts, amino acids, enzymes and other proteins, abrasives, odor control agents, conditioning agents, moisturizers, humectants, occlusive agents, skin lipid fluidizers, lipophilic actives, hydrophilic materials, pearlizers, opacifying agents, and mixtures thereof.

In at least one embodiment, the carrier is anhydrous.

In at least one embodiment, the carrier is hydrophilic.

In at least one embodiment, the carrier is hydrophobic.

Embodiments of the disclosure may also provide a method for preventing or treating inflammation in or on skin of a subject. The method may include contacting any of the personal care compositions disclosed herein with surfaces of the skin of the subject in need thereof.

Embodiments of the disclosure may also provide a method for promoting or facilitating cell repair in or on skin of a subject. The method may include contacting any of the personal care compositions disclosed herein with surfaces of the skin of the subject in need thereof.

Embodiments of the disclosure may also provide a method for whitening skin of a subject. The method may include contacting any of the personal care compositions disclosed herein with surfaces of the skin of the subject in need thereof.

Embodiments of the disclosure may also provide a method for preparing a personal care composition. The method may include contacting a naringin:zinc complex with a carrier.

In at least one embodiment, the personal care composition is an antiperspirant, a deodorant, a body wash, a shower gel, a soap, a face wash, a shampoo, a hair conditioner, a lotion, or a cosmetic.

Further areas of applicability of the present disclosure will become apparent from the detailed description provided hereinafter. It should be understood that the detailed description and specific examples, while indicating some typical aspects of the disclosure, are intended for purposes of illustration only and are not intended to limit the scope of the disclosure.

DETAILED DESCRIPTION

The following description of various typical aspect(s) is merely exemplary in nature and is in no way intended to limit the disclosure, its application, or uses.

As used throughout, ranges are used as shorthand for describing each and every value that is within the range. Any value within the range may be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Additionally, all numerical values are "about" or "approximately" the indicated value, and take into account experimental error and variations that would be expected by a person having ordinary skill in the art. It should be appreciated that all numerical values and ranges disclosed herein are approximate values and ranges, whether "about" is used in conjunction therewith. It should also be appreciated that the term "about," as used herein, in conjunction with a numeral refers to a value that may be ±0.01% (inclusive), ±0.1% (inclusive), ±0.5% (inclusive), ±1% (inclusive) of that numeral, ±2% (inclusive) of that numeral, ±3% (inclusive) of that numeral, ±5% (inclusive) of that numeral, ±10% (inclusive) of that numeral, or ±15% (inclusive) of that numeral. It should further be appreciated that when a numerical range is disclosed herein, any numerical value falling within the range is also specifically disclosed.

The present inventors have surprisingly and unexpectedly discovered that incorporating a naringin:zinc complex in personal care compositions may decease levels of an inflammation and irritation biomarker, namely IL-la, in cells and tissues. The present inventors have also surprisingly and unexpectedly discovered that personal care compositions including a naringin:zinc complex may facilitate cell repair and regeneration.

Compositions

Compositions disclosed herein may be or include a personal care product or a personal care composition thereof. For example, compositions disclosed herein may be a personal care composition a personal care product, or form a portion of the personal care composition or the personal care product. In an exemplary implementation, the compositions disclosed herein are personal care composition including a carrier and a naringin:zinc complex. The compositions including the carrier and an effective amount of the naringin:zinc complex may be capable of or configured to provide one or more benefits to cells and/or tissue (e.g., skin). For example, the personal care compositions disclosed herein may be capable of or configured to facilitate, promote, or otherwise improve skin regeneration of a user or subject in need thereof. In another example, the personal care compositions disclosed herein may be capable of or configured to facilitate, promote, or otherwise improve one or more anti-inflammatory responses of the skin of a user or subject in need thereof.

Naringin:Zinc Complex

The personal care composition may include a naringin:zinc complex. The naringin:zinc complex may have a naringin to zinc molar ratio of 1:1, 2:1, or 3:1. In a preferred implementation, the naringin:zinc complex has a naringin to zinc molar ratio of 2:1, and may be represented by chemical formula (I).

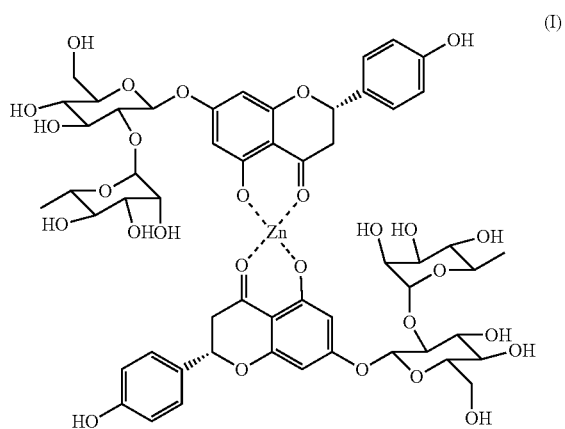

The naringin:zinc complex may have a melting point greater than or equal to 200° C. The naringin:zinc complex may also have a melting point less than or equal to about 305° C. For example, the melting point of the naringin:zinc complex may be from about 200° C., about 205° C., about 210° C., about 215° C., about 220° C., about 225° C., about 230° C., about 235° C., about 240° C., about 245° C., or about 250° C. to about 255° C., about 260° C., about 265° C., about 270° C., about 275° C., about 280° C., about 285° C., about 290° C., about 295° C., about 300° C., or about 305° C. In another example, the melting point of the naringin:zinc complex may be from about 200° C. to about 305° C., about 205° C. to about 300° C., about 210° C. to about 295° C., about 215° C. to about 290° C., about 220° C. to about 285° C., about 225° C. to about 280° C., about 230° C. to about 275° C., about 235° C. to about 270° C., about 240° C. to about 265° C., about 245° C. to about 260° C., or about 250° C. to about 255° C. In yet another example, the naringin:zinc complex may have a melting point greater than or equal to 200° C., greater than or equal to 205° C., greater than or equal to 210° C., greater than or equal to 215° C., greater than or equal to 220° C., greater than or equal to 225° C., greater than or equal to 230° C., greater than or equal to 235° C., greater than or equal to 240° C., greater than or equal to 245° C., or greater than or equal to 250° C. to greater than or equal to 255° C., greater than or equal to 260° C., greater than or equal to 265° C., greater than or equal to 270° C., greater than or equal to 275° C., greater than or equal to 280° C., greater than or equal to 285° C., greater than or equal to 290° C., greater than or equal to 295° C., greater than or equal to 300° C., or greater than or equal to 305° C. In an exemplary implementation, the naringin:zinc complex has a melting point greater than or equal to 230° C.

The naringin:zinc complex may have a diffusion coefficient in dimethyl sulfoxide (DMSO) at 25° C. of from about 2.3E−11 $m^2$/s to about 3.2E−11 $m^2$/s. For example, the naringin:zinc complex may have a diffusion coefficient in dimethyl sulfoxide (DMSO) at 25° C. of from about 2.3E−11 $m^2$/s, about 2.4E−11 $m^2$/s, about 2.5E−11 $m^2$/s, about 2.6E−11 m²/s, or about 2.7E−11 m²/s to about 2.8E−11 m²/s, about 2.9E−11 m²/s, about 3.0E−11 m²/s, about 3.1E−11 m²/s, or about 3.2E−11 m²/s. In another example, the naringin:zinc complex may have a diffusion coefficient in dimethyl sulfoxide (DMSO) at 25° C. of from about 2.3E−11 m²/s to about 3.2E−11 m²/s, about 2.4E−11 m²/s to about 3.1E−11 m²/s, about 2.5E−11 m²/s to about 3.0E−11 m²/s, about 2.6E−11 m²/s to about 2.9E−11 m²/s, or about 2.7E−11 m²/s to about 2.8E−11 m²/s.

The naringin:zinc complex may be present in the personal care composition in an effective amount or a therapeutically effective amount. As used herein, the expression or term "effective amount" may refer to an amount of the naringin:zinc complex sufficient to elicit a response (e.g., biological, medical, etc.) of a tissue, system, animal, or human that is being sought. For example, the naringin:zinc complex may be present in the personal care composition in an effective amount to initiate, improve, or otherwise facilitate skin regeneration. In another example, the naringin:zinc complex may be present in the personal care composition in an effective amount to provide an anti-inflammatory effect to a tissue (e.g., skin), system, animal, or human. In yet another example, the naringin:zinc complex may be present in the personal care composition in an effective amount to provide antioxidant, whitening, and/or collagen-boosting effects to a tissue (e.g., skin), system, animal, or human.

In at least one implementation, the naringin:zinc complex may be present in the personal care composition in an amount of from about 0.01 weight % to about 5 weight %, based on a total weight of the personal care composition. For example, the naringin:zinc complex may be present in the personal care composition in an amount of from about 0.01 weight %, about 0.1 weight %, about 0.2 weight %, about 0.3 weight %, about 0.4 weight %, about 0.5 weight %, about 0.6 weight %, about 0.7 weight %, about 0.8 weight %, about 0.9 weight %, about 1 weight %, about 1.2 weight %, about 1.4 weight %, about 1.6 weight %, about 1.8 weight %, about 2 weight %, about 2.2 weight %, or about 2.4 weight % to about 2.6 weight %, about 2.8 weight %, about 3 weight %, about 3.2 weight %, about 3.4 weight %, about 3.6 weight %, about 3.8 weight %, about 4 weight %, about 4.1 weight %, about 4.2 weight %, about 4.3 weight %, about 4.4 weight %, about 4.5 weight %, about 4.6 weight %, about 4.7 weight %, about 4.8 weight %, about 4.9 weight %, or about 5 weight %, based on a total weight of the personal care composition. In another example, the naringin:zinc complex may be present in the personal care composition in an amount of from about 0.01 weight % to about 5 weight %, about 0.1 weight % to about 4.9 weight %, about 0.2 weight % to about 4.8 weight %, about 0.3 weight % to about 4.7 weight %, about 0.4 weight % to about 4.6 weight %, about 0.5 weight % to about 4.5 weight %, about 0.6 weight % to about 4.4 weight %, about 0.7 weight % to about 4.3 weight %, about 0.8 weight % to about 4.2 weight %, about 0.9 weight % to about 4.1 weight %, about 1 weight % to about 4 weight %, about 1.2 weight % to about 3.8 weight %, about 1.4 weight % to about 3.6 weight %, about 1.6 weight % to about 3.4 weight %, about 1.8 weight % to about 3.2 weight %, about 2 weight % to about 3 weight %, about 2.2 weight % to about 2.8 weight %, or about 2.4 weight % to about 2.6 weight %, based on a total weight of the personal care composition The naringin:zinc complex may be prepared by combining, mixing, reacting, or otherwise contacting naringin and zinc (i.e., zinc ions) or a source of zinc with one another in a suitable medium or solvent. For example, the naringin:zinc complex may be prepared by contacting the naringin and a source of zinc with one another in an organic solvent. Illustrative organic solvents may be or include, but are not limited to, methanol, ethanol, propanol, methylene glycol, ethylene glycol, propylene glycol, and the like, and mixtures or combinations thereof. In another example, the naringin:zinc complex may be prepared by contacting the naringin and the source of zinc with one another in an aqueous solvent, such as water.

The naringin:zinc complex may be prepared by heating the mixture of the naringin, the source of zinc, and/or the suitable medium or solvent to a temperature of from about 20° C. to about 80° C. For example, the naringin:zinc complex may be prepared by heating the mixture of the naringin, the source of zinc, and the suitable medium or solvent to a temperature of from about 20° C., about 25° C., about 30° C., about 35° C., about 40° C., or about 45° C. to about 55° C., about 60° C., about 65° C., about 70° C., about 75° C., or about 80° C. In another example, the naringin:zinc complex may be prepared by heating the mixture of the naringin, the source of zinc, and the suitable medium or solvent to a temperature of from about 20° C. to about 80° C., about 25° C. to about 75° C., about 30° C. to about 70° C., about 35° C. to about 65° C., about 40° C. to about 60° C., or about 45° C. to about 55° C. In yet another example, the naringin:zinc complex may be prepared by heating the mixture of the naringin, the source of zinc, and the suitable medium or solvent to a temperature of at least 20° C., at least 25° C., at least 30° C., at least 35° C., at least 40° C., at least 45° C., at least 50° C., at least 55° C., at least 60° C., at least 65° C., at least 70° C., or at least 75° C.

The pH of the mixture including the naringin, the source of zinc, and/or the suitable medium or solvent may be adjusted. For example, the pH of the mixture including the naringin, the source of zinc, and/or the suitable medium or solvent may be increased or decreased through the addition of a base or an acid, respectively. In at least one implementation, the pH of the mixture including the naringin, the source of zinc, and/or the suitable medium or solvent may be adjusted to about 7, about 8, about 9, about 10, or about 11. In another example, the naringin-zinc complex may be prepared in a pH of about 7, about 8, about 9, about 10, or about 11.

The zinc or zinc ions may be provided by one or more zinc ion sources. For example, the zinc ions may be provided by one or more zinc salts. Illustrative zinc ion sources may be or include, but are not limited to, zinc oxide, zinc acetate, zinc chloride, zinc lactate, tetrabasic zinc chloride, zinc carbonate, zinc nitrate, zinc citrate, zinc bisglycinate, zinc phosphate, and the like, and mixtures or combinations thereof. It should be appreciated that zinc oxide and tetrabasic zinc chloride are insoluble in water, but readily form complexes with naringin in water upon the addition of heat. In a preferred implementation, the zinc ion source includes at least one of zinc acetate, zinc oxide, zinc chloride, zinc lactate, zinc citrate, zinc nitrate, and mixtures or combinations thereof Carrier or Excipient The personal care composition may include the naringin:zinc complex dispersed in, mixed with, dissolved in, combined with, or otherwise contacted with the carrier. In at least one implementation, the carrier may be capable of or configured to store, entrain, or otherwise contain the naringin:zinc complex, and deliver the naringin:zinc complex. It should be appreciated that the components or contents of the carrier and the respective amount of each of the components of the carrier may be at least partially determined by the type or use of the personal care product or the composition thereof. Illustrative personal care products or compositions thereof that may include the naringin:zinc complex include, but are not limited to, antiperspirants, deodorants, body washes, shower gels, soaps, including bar soaps and liquid soaps (e.g., liquid hand soaps), face washes, shampoos, hair conditioners, lotions, moisturizers, serums, spot treatments, cosmetics, and the like.

In at least one implementation, the personal care product or the composition thereof may be a skin care product. Illustrative skin care product may be or include, but are not limited to, a lotion, a cosmetic, a sunscreen, and the like. The carrier of the skin care product may include, but is not limited to, any one or more of surfactants, conditioning agents, moisturizers, sunscreens, UV absorbers, antioxidants, enzymes and other proteins, vitamins, antibacterial agents, odor reducing agents, steroids, anti-inflammatory agents, naturally and non-naturally occurring humectants, skin lipid fluidizers, occlusive agents, amino acids, physical and chemical exfoliants, skin whiteners, anti-aging, antiperspirant actives, and the like, and mixtures thereof.

In at least one implementation, the personal care product or the composition thereof may be a hair care product. Illustrative hair care products may be or include, but are not limited to, a shampoo (e.g., dry and wet shampoo), a conditioner (e.g., leave in conditioner), hair spray, gels, and the like. The carrier for the hair care product may include, but is not limited to, any one or more of surfactants, colorants, denaturants, film forming polymers, conditioning agents, fixatives, hair color stabilizers, anti-inflammatory agents, antioxidants, moisturizers, enzymes and other proteins, vitamins, antidandruff agents, sunscreen agents, and mixtures thereof. Illustrative conditioning agents may include, but are not limited to, any one or more of silicones (e.g., silicone oils, cationic silicones, silicone gums, high refractive silicones, silicone resins, etc.), and organic conditioning oils (e.g., hydrocarbon oils, polyolefins, fatty esters, etc.). Illustrative anti-dandruff agents may include, but are not limited to, pyridinethione salts, selenium sulfide, particulate sulfur, and the like, and mixtures thereof. Illustrative anti-inflammatories may include, but are not limited to, glucocorticoids, nonsteroidal anti-inflammatories, and the like, and mixtures or combinations thereof. Illustrative colorants may include, but are not limited to, non-oxidative dyes, such as "direct action dyes," metallic dyes, metal chelate dyes, fiber/fibre reactive dyes, other synthetic and natural dyes, and the like, and mixtures or combinations thereof. Illustrative sunscreen agents may include, but are not limited to, 2-ethylhexyl p-methoxycinnamate, 2-ethylhexyl N,N-dimethyl-p-aminobenzoate, p-aminobenzoic acid, 2-phenylbenzimidazole-5-sulfonic acid, octocrylene, oxybenzone, homomenthyl salicylate, octyl salicylate, 4,4'-methoxy-t-butyldibenzoylme-thane, 4-isopropyl dibenzoylmethane, 3-benzylidene camphor, 3-(4-methylbenzylidene) camphor, titanium dioxide, zinc oxide, silica, iron oxide, and the like, and mixtures or combinations thereof. Illustrative vitamins may include, but are not limited to, Vitamin E, panthenol, and the like, and mixtures or combinations thereof.

In at least one implementation, the personal care product or the composition thereof may be an antiperspirant or deodorant. The carrier for the antiperspirant or deodorant may include, but is not limited to, any one or more of fragrances, alcohols, antimicrobial agents, antiperspirant salts, odor reducing agents, moisturizers, other components as discussed above for skin and hair care compositions, and mixtures or combinations thereof. Illustrative antimicrobial agents may include, but are not limited to, primary oleamine salt of piroctone, metal salts of piroctone acid (such as aluminum, sodium, potassium, zirconium, calcium and zinc metal salts), triclosan, zinc phenolsulfonate, heavy metal salts of 1-hydroxy pyridinethione (such as zinc pyrithione, magnesium pyrithione, and aluminum pyrithione), bacteriostatic quaternary ammonium compounds (such as cetyltrimethyl ammonium bromide, cetyl pyridinium chloride, benzethonium chloride, and sodium N-lauryl-sarcosine), carbonate and bicarbonate salts, and the like, and mixtures or combinations thereof. Illustrative antiperspirant salts may include, but are not limited to, poly-valent metal salts and complexes thereof, such as aluminum halides, aluminum hydroxy-halides, zirconyl oxyhalides, zirconyl hydroxy-halides, zinc compounds, such as zinc phenylsulfonate, zinc glycinate and zinc pyrithione, and the like, and mixtures or combinations thereof. Illustrative complexes may be or include, but are not limited to, amino acids (e.g., glycine) forming antiperspirant actives commonly known as "ZAG," including aluminum, zirconium, and chlorine having an Al:Zr ratio of about 1.67 to about 12.5 and a Metal:C1 ratio of about 0.73 to about 1.93. Illustrative odor reducing agents may include, but are not limited to, sulfur precipitating agents, such as copper gluconate, zinc citrate, zinc gluconate, and the like, and mixtures or combinations thereof.

In at least one implementation, the personal care product or the composition thereof may be a personal hand and/or body cleansing composition or a personal hand and/or body conditioning composition. Illustrative personal hand and/or body cleansing or conditioning compositions may include, but are not limited to, liquid soaps, bar soaps, body washes, lotions, and the like. The carrier for the personal hand and/or body cleansing composition or the personal hand and/or body conditioning composition may include, but is not limited to, any one or more of fragrances, essential oils, emulsifying agents, thickening agents, colorants, surfactants, natural actives, therapeutic actives, stain prevention actives, antimicrobial agents, vitamins, natural extracts, amino acids, enzymes or other proteins, abrasives, odor control agents, conditioning agents, moisturizers, humectants, occlusive agents, skin lipid fluidizers, lipophilic actives, hydrophilic materials, pearlizers, opacifying agents, and the like, and mixtures or combinations thereof, in addition to the other carrier components as discussed above.

The carrier may be hydrophilic or hydrophobic. The carrier may be anhydrous. The carrier may be a liquid or a solid at room temperature. The carrier may have a viscosity of from about 2,000 centipoise (cP) to about 100,000 cP. For example, the carrier for a shower gel may have a viscosity of from about 2,000 cP to about 16,000 cP. In another example, the carrier for a lotion may have a viscosity of from about 10,000 cP to about 100,000 cP. Accordingly, it should be appreciated that the viscosity of the carrier may vary and may at least partially depend on the type of personal care composition.

Unless otherwise specifically identified, the ingredients for use in the compositions and formulations of the present invention are preferably cosmetically acceptable ingredients. By "cosmetically acceptable" is meant suitable for use in a formulation for topical application to human skin. A cosmetically acceptable excipient, for example, is an excipient which is suitable for external application in the amounts and concentrations contemplated in the formulations of this invention, and includes for example, excipients which are "Generally Recognized as Safe" (GRAS) by the United States Food and Drug Administration.

Methods

The present disclosure may provide methods for preparing a naringin:zinc complex having a 2:1 mole ratio of naringin to zinc. The method may include contacting naringin and zinc or a source of zinc in a suitable medium, such as water or an organic solvent. The method may also include heating the naringin and zinc or the source of zinc in the suitable medium. The method may further include adjusting the pH of the suitable medium including the naringin and zinc or the source of zinc.

The present disclosure may also provide methods for preparing a personal care composition. The method may include contacting a naringin:zinc complex with a carrier.

The present disclosure may also provide methods for reducing or treating inflammation of tissue (e.g., skin). The method may include contacting the tissue (e.g., surface of the skin) with a naringin:zinc complex. The method may also include combining or otherwise contacting a naringin:zinc complex with a carrier to prepare a personal care composition, and contacting the tissue with the personal care composition.

The present disclosure may also provide methods for reducing irritation of tissue (e.g., skin). The method may include contacting the tissue (e.g., surface of the skin) with a naringin:zinc complex. The method may also include combining or otherwise contacting a naringin:zinc complex with a carrier to prepare a personal care composition, and contacting the tissue with the personal care composition.

The present disclosure may also provide methods for promoting or facilitating cell repair or regeneration of tissue (e.g., skin). The method may include contacting the tissue (e.g., surface of the skin) with a naringin:zinc complex. The method may also include combining or otherwise contacting a naringin:zinc complex with a carrier to prepare a personal care composition, and contacting the tissue with the personal care composition.

The present disclosure may further provide a use of a personal care composition including a carrier and a naringin:zinc complex for reducing or treating inflammation of tissue (e.g., skin).

The present disclosure may further provide a use of a personal care composition including a carrier and a naringin:zinc complex for reducing irritation of tissue (e.g., skin).

The present disclosure may further provide a use of a personal care composition including a carrier and a naringin:zinc complex for promoting or facilitating repair or regeneration of tissue (e.g., skin).

The present disclosure may further provide a method of making a personal care composition for reducing or treating inflammation of tissue. The method may include combining or otherwise contacting a naringin:zinc complex with a carrier to prepare the personal care composition.

The present disclosure may further provide a method of making a personal care composition for reducing irritation of tissue. The method may include combining or otherwise contacting a naringin:zinc complex with a carrier to prepare the personal care composition.

The present disclosure may further provide a method of making a personal care composition for promoting or facilitating cell repair or regeneration of tissue. The method may include combining or otherwise contacting a naringin:zinc complex with a carrier to prepare the personal care composition.

EXAMPLES

The examples and other implementations described herein are exemplary and not intended to be limiting in describing the full scope of compositions and methods of this disclosure. Equivalent changes, modifications and variations of specific implementations, materials, compositions and methods may be made within the scope of the present disclosure, with substantially similar results.

Example 1

The anti-inflammatory properties of the naringin:zinc complex was evaluated by conducting an IL-1a assay using HaCaT cells. To evaluate the anti-inflammatory properties, HaCaT cells were grown into 80% confluency and pretreated for 24 hours with 1 mL of each of the following samples: (1) a culture media (control); (2) 0.001% naringin:zinc complex; and (3) 0.001% naringin alone. To prepare the 0.001% naringin-zinc complex and the 0.001% naringin alone, each of the naringin:zinc complex and the naringin were prepared in stock solutions of 1% DMSO/PBS and diluted to the target concentration using culture media.

After pretreating the HaCaT cells, the cells were stressed with 0.01% SDS for 15 minutes before adding another 1 mL of each of the samples (1)-(3). Each of the HaCaT cells were used to prepare cell supernatants, which were used for IL-1a assays with IL-1a ELISA kits. The results of the IL-1a assay are summarized in Table 1.

TABLE 1

| IL-1a Assay[1] | | |
|---|---|---|
| Sample | pg/mL | Std Dev |
| Control (1) Prior to SDS Stress | 1.7 | 0.6 |
| Control (1) | 8.3 | 1.0 |
| 0.001% Naringin:Zinc Complex (2) | 5.2 | 1.9 |
| Naringin (3) | 6.6 | 1.3 |

[1]IL-1a levels were normalized by cell viability

It should be appreciated that IL-1a is one of the main biomarkers for inflammation/irritation. It should further be appreciated that SDS is a well-known inducer for skin irritation. As indicated in Table 2, treatment with 0.01% SDS on the control resulted in a four-fold increase in IL-1a levels from 1.7 pg/mL to 8.3 pg/mL. As further illustrated in Table 2, the addition of the naringin:zinc complex prior to and after SDS stress treatment resulted in a reduction of the inflammation biomarker as compared to the control. The results also surprisingly and unexpectedly indicate that the naringin:zinc complex exhibited relatively lower IL-1a as compared to the naringin alone (3).

Example 2

The soothing properties or benefits of the naringin:zinc complex were evaluated in an exemplary carrier. Particularly, the soothing properties were evaluated by incorporating the naringin:zinc complex in an amount of 0.5% in a skin cleansing carrier. EpiDerm™ tissue obtained from MatTek Corporation was treated for 1 hour with either (4) the skin cleansing carrier alone; or (5) the skin cleansing carrier including the naringin:zinc complex. After treatment, each of the tissue samples were washed six to seven times with phosphate buffered saline (PBS) and incubated in a cultured media for at least 18 hours. The supernatants were sampled for IL-1a levels, and the results are summarized in Table 2.

TABLE 2

IL-1a Assay of EpiDerm ™ tissue[2]

| Sample | pg/mL | Std Dev |
| --- | --- | --- |
| Control | 32.8 | 1.0 |
| Carrier (4) | 76.8 | 5.9 |
| Carrier + Naringin:Zinc Complex (5) | 53.1 | 12.6 |

[2]IL-1a levels were normalized by Total Protein Concentration

As illustrated in Table 2, the naringin:zinc complex exhibited significantly lower IL-1a levels, which represented irritation potential. The significant reduction of the IL-1a, which were both surprising and unexpected, further confirmed the anti-inflammatory properties of the complex.

Example 3

The cell regeneration function or properties of the naringin:zinc complex were evaluated via a scratch assay using human epidermal keratinocyte cells obtained from Thermal Fisher Scientific of Gaithersburg, Md. Particularly, monolayers of keratinocyte cells were gown to full confluency in separate wells, and each well was scratched with a 1000 μl tip to create a cell-free gap. Each of the wells with the cell-free gap was then washed with 1 mL of PBS twice to remove any dead floating cells. Each of the wells were treated/incubated with 1 mL of each of the following samples: (6) culture media (control); (7) 0.001% naringin:zinc complex; (8) 0.001% naringin alone; (9) 0.000065% zinc oxide (ZnO); and (10) naringin and zinc oxide mixture. Distance measurements of the gap were taken every 24 hours until the gaps fully closed. The distance measurements of each of the respective gaps before and after treatment/incubation were taken using a microscope (OLYMPUS® IX71), and the results are summarized in Table 3.

TABLE 3

Cell Migration of Keratinocytes (% Active)

| Sample | pg/mL | P value vs. Control |
| --- | --- | --- |
| Control (6) | 47 | — |
| 0.001% Naringin:Zinc Complex (7) | 81 | 0.0001 |
| 0.001% Naringin (8) | 58 | 0.7457 |
| 0.000065% ZnO (9) | 59 | 0.0454 |
| Naringin + ZnO mixture (10) | 63 | 0.0405 |

Table 3 illustrates the percentage of gap closure versus the starting gap distance. It should be appreciated that a relatively higher value of the percentage of gap closure indicates a relatively greater repair or regeneration function. While each of the samples, except naringin alone (8), demonstrated statistically significant repair or regeneration as compared to the control (6) ($p<0.05$), it was surprisingly and unexpectedly discovered that the naringin:zinc complex exhibited a relatively greater and statistically significant increase in the repair or regeneration function as compared to the remaining samples. It was further surprisingly and unexpectedly discovered that the naringin and zinc oxide mixture (10), including the naringin and the zinc oxide in the same molar ratio as the naringin-zinc complex (7), exhibited relatively lower repair activity as compared to the naringin-zinc complex (7). These results supported the synergistic relationship between the naringin and zinc in the naringin:zinc complex (7) and are nothing short of surprising and unexpected.

The present disclosure has been described with reference to exemplary implementations. Although a limited number of implementations have been shown and described, it will be appreciated by those skilled in the art that changes may be made in these implementations without departing from the principles and spirit of the preceding detailed description. It is intended that the present disclosure be construed as including all such modifications and alterations insofar as they come within the scope of the appended claims or the equivalents thereof.

What is claimed is:

1. A personal care composition comprising a cosmetically acceptable carrier; and
   a naringin:zinc complex having a 2:1 naringin to zinc molar ratio wherein the naringin:zinc complex is represented by chemical formula (I):

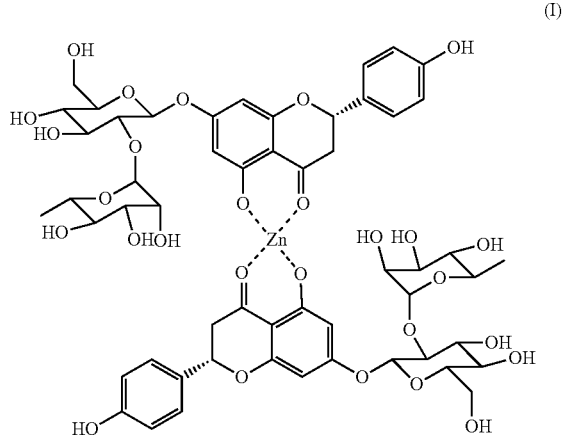

wherein the personal care composition is an antiperspirant, a deodorant, a body wash, a shower gel, a soap, a face wash, a shampoo, a hair conditioner, a lotion, a moisturizer, a serum, or a cosmetic.

2. The personal care composition according to claim 1, wherein the personal care composition is a body wash, a shower gel, a soap, a face wash, a lotion, a moisturizer, a serum, or a cosmetic, and wherein the carrier comprises at least one of surfactants, conditioning agents, moisturizers, sunscreens, UV absorbers, antioxidants, enzymes and other proteins, vitamins, antibacterial agents, odor reducing agents, steroids, anti-inflammatory agents, naturally and non-naturally occurring humectants, skin lipid fluidizers, occlusive agents, amino acids, physical and chemical exfoliates, skin whiteners, anti-aging, antiperspirant actives, and mixtures thereof.

3. The personal care composition according to claim 1, wherein the personal care composition is a shampoo or a hair conditioner, and wherein the carrier comprises at least one of surfactants, colorants, denaturants, film forming polymers, conditioning agents, fixatives, hair color stabilizers, anti-inflammatory agents, antioxidants, moisturizers, enzymes and other proteins, vitamins, anti-dandruff agents, sunscreen agents, and mixtures thereof.

4. The personal care composition according to claim 1, wherein the personal care composition is an antiperspirant or a deodorant, and wherein the carrier comprises at least one of fragrances, alcohols, antimicrobial agents, antiperspirant salts, odor reducing agents, moisturizers, and mixtures thereof.

5. A method for treating inflammation in skin of a subject or for promoting or facilitating cell repair in skin of a subject, comprising contacting a personal care composition comprising a cosmetically acceptable carrier; and a naringin:zinc complex having a 2:1 naringin to zinc molar ratio wherein the naringin:zinc complex is represented by chemical formula (I):

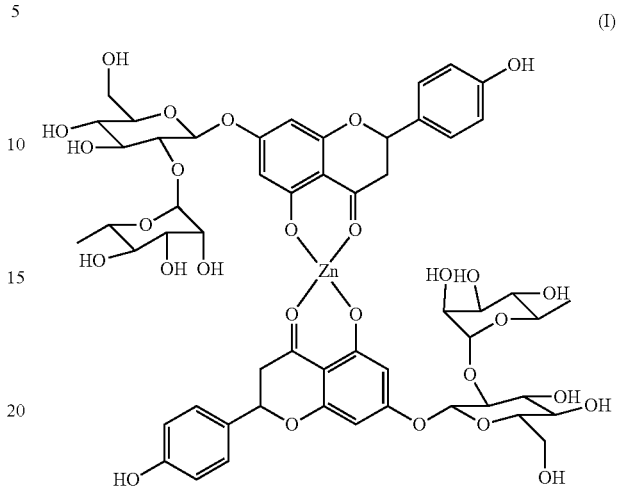

with surfaces of the skin of the subject in need thereof, wherein the personal care composition is an antiperspirant, a deodorant, a body wash, a shower gel, a soap, a face wash, a shampoo, a hair conditioner, a lotion, or a cosmetic.

* * * * *